US010717683B2

(12) United States Patent
McCarthy

(10) Patent No.: US 10,717,683 B2
(45) Date of Patent: Jul. 21, 2020

(54) HOUSING FOR A WORM FARM

(71) Applicant: HANDELA PTY LTD, Ashburton (AU)

(72) Inventor: Tony McCarthy, Ashburton (AU)

(73) Assignee: HANDELA PTY LTD, Ashburton (AU)

( * ) Notice: Subject to any disclaimer, the term of this patent is extended or adjusted under 35 U.S.C. 154(b) by 216 days.

(21) Appl. No.: 15/573,798

(22) PCT Filed: May 13, 2016

(86) PCT No.: PCT/AU2016/050361
§ 371 (c)(1),
(2) Date: Nov. 13, 2017

(87) PCT Pub. No.: WO2016/179662
PCT Pub. Date: Nov. 17, 2016

(65) Prior Publication Data
US 2018/0111885 A1     Apr. 26, 2018

(30) Foreign Application Priority Data

May 13, 2015   (AU) ................................ 2015901738

(51) Int. Cl.
*A01K 67/033* (2006.01)
*C05F 17/05* (2020.01)
(Continued)

(52) U.S. Cl.
CPC .......... *C05F 17/05* (2020.01); *A01K 67/0332* (2013.01); *C05F 3/06* (2013.01);
(Continued)

(58) Field of Classification Search
CPC .............. A01K 67/0332; A01K 63/003; A01K 67/033; C05F 17/0009; C05F 17/0205;
(Continued)

(56) References Cited

U.S. PATENT DOCUMENTS 2,050,814 A * 8/1936 Steiger ................... B65D 15/24
                                                    217/5
3,566,836 A * 3/1971 Elfert ................. A01K 67/0332
                                                    119/6.7
(Continued)

FOREIGN PATENT DOCUMENTS

CN         202112171 U     1/2012
FR         2784880 B2      1/2001
(Continued)

OTHER PUBLICATIONS

MR_YAN, "5-gallon-bucket X worm inn—call it an F1 hybrid," GardenWeb Forums Website, Available Online at http://forums.gardenweb.com/discussions/2208705/5-gallon-bucket-x-worm-inn-call-it-an-f1-hybrid, Dec. 26, 2011, 5 pages.
(Continued)

*Primary Examiner* — Claude J Brown
(74) *Attorney, Agent, or Firm* — Alleman Hall Creasman & Tuttle LLP

(57) ABSTRACT

A housing for a worm farm includes a composting cavity that, in use of the housing, is to contain worms, bedding material and/or organic waste, the composting cavity being defined by a floor having openings through which castings can pass, and one or more side walls that extend around the floor. A support structure supports the floor and the side walls above a ground surface. A cover locates on the side walls and extend over the composting cavity, and is movable to enable access to the composting cavity. A castings receptacle is movable between an operative position and at least one displaced position.

12 Claims, 14 Drawing Sheets

(51) Int. Cl.
*C05F 17/95* (2020.01)
*C05F 17/907* (2020.01)
*C05F 17/964* (2020.01)
*C05F 3/06* (2006.01)

(52) U.S. Cl.
CPC ............ *C05F 17/907* (2020.01); *C05F 17/95* (2020.01); *C05F 17/964* (2020.01); *Y02A 40/208* (2018.01); *Y02P 20/145* (2015.11); *Y02W 30/43* (2015.05)

(58) Field of Classification Search
CPC .... C05F 17/0247; C05F 17/0258; C05F 3/06; C05F 17/02; C05F 17/05; C05F 17/907; C05F 17/95; C05F 17/964; Y02A 40/208
USPC .......................................................... 119/6.7
See application file for complete search history.

(56) References Cited

U.S. PATENT DOCUMENTS

| | | | | |
|---|---|---|---|---|
| 3,928,950 | A * | 12/1975 | Beynon | E04B 9/10 52/506.07 |
| 3,961,603 | A * | 6/1976 | Gaddie, Sr. | A01K 67/0332 119/6.7 |
| 4,643,610 | A * | 2/1987 | Bien | F16B 37/043 403/326 |
| 4,797,020 | A * | 1/1989 | Winston | E04B 1/2604 403/230 |
| 4,815,416 | A * | 3/1989 | Wolff | A01K 97/04 119/6.7 |
| 6,576,462 | B2 | 6/2003 | Thompson | |
| 7,998,728 | B2 | 8/2011 | Rhoads et al. | |
| 8,642,324 | B2 * | 2/2014 | Bell | A01K 67/0332 435/290.1 |
| 8,951,787 | B1 * | 2/2015 | O'Donnell | C05F 17/0009 435/290.1 |
| 2002/0115199 | A1 * | 8/2002 | Thompson | A01K 67/0332 435/290.1 |
| 2003/0059931 | A1 * | 3/2003 | Gitt | C05F 17/0205 435/290.1 |
| 2010/0273251 | A1 * | 10/2010 | Rhoads | C05F 17/0009 435/290.1 |
| 2012/0214223 | A1 * | 8/2012 | Hughes | A01K 67/0332 435/287.1 |
| 2012/0244611 | A1 * | 9/2012 | Branham | C05F 17/0009 435/290.1 |
| 2013/0118410 | A1 | 5/2013 | Berkson | |

FOREIGN PATENT DOCUMENTS

| | | | | |
|---|---|---|---|---|
| WO | 0032540 | A1 | 6/2000 | |
| WO | 0053543 | A1 | 9/2000 | |
| WO | WO-0053543 | A1 * | 9/2000 | .......... C05F 17/0009 |
| WO | 2012156868 | A1 | 11/2012 | |
| WO | WO-2015173804 | A1 * | 11/2015 | |

OTHER PUBLICATIONS

"Texas Red Worms," Texas Red Worms Website, Retrieved Online at http://web.archive.org/web/20140116050145/http://texasredworms.com/tag/worm-bin, Available as Early as Apr. 28, 2013, 10 pages.
ISA Australian Patent Office, International Search Report Issued in PCT Application No. PCT/AU2016/050361, dated Jun. 30, 2016, WIPO, 6 pages.

* cited by examiner ated, lifting the heavy working trays can be difficult and may even cause injury to the farmer. Furthermore, it is likely that any worms falling into the bottom tray will eventually die

HOUSING FOR A WORM FARM

This application is a national phase of International Application Serial No. PCT/AU2016/050361, entitled A HOUSING FOR A WORM FARM, filed May 13, 2016, which in turn claims priority to Australian Patent Application Serial No. 2015901738, entitled A HOUSING FOR A WORM FARM, filed May 13, 2015.

FIELD OF THE INVENTION

The present invention relates to a housing for a worm farm.

BACKGROUND

Composted organic material is a fertilizer that can be used to return valuable nutrients to the earth for reuse by living plants. Composting waste organic material is also more environmentally friendly, compared with collecting and storing the waste in landfill.

It is particularly efficient to compost waste organic material domestically, as the composted material can be used in fertilizing plants at the site at which the waste organic material is "created" (i.e. at a residential dwelling). There are two main types of compost farms used in domestic, and community settings (such as kindergartens, schools, community gardens, etc.), these being:

aerobic, which use living organisms to consume decomposing organic matter in an environment of moist bedding material and oxygen; and anaerobic, which use the activity of microorganisms feeding on carbon rich material in the absence of oxygen.

Vermicomposting is an aerobic composting process that uses composting earthworms (such as Red, Tiger and Blue worms) to break down the organic matter. Vermicompost processes have the advantage of being able to process organic waste material quickly and efficiently because the worms induce aeration and form moisture drainage tunnels as they move through the bedding material, which enables quicker production of composted organic materials (known as "vermicast" or "castings"). Further, in a well functioning worm farm, the worm population can increase over time, which further increases the volume of organic waste that can be composted by the worm farm.

It is known to construct a "tiered" or "stackable" worm farm housing with a bottom tray to collect liquid (sometimes referred to as "worm tea"). A first working tray is nested in the bottom tray, and this is filled with a bedding material of soil and organic waste material for the worms to compost. Once the first working tray is almost full, a part of the bedding material is transferred to a second working tray which is then nested in the first. The worms gradually move from the first working tray into the second, leaving castings (in other words, the composted organic material) behind. The castings are then available for use as a fertilizer. While this type of system is functional, it has significant drawbacks. These include that the second working tray must be lifted from the tier in order to access the castings in the first working tray. In addition, the first working tray contains compacted castings, and users often carry the full first working tray to the site to be fertilized. As will be appreciated, lifting the heavy working trays can be difficult and may even cause injury to the farmer. Furthermore, it is likely that any worms falling into the bottom tray will eventually die and, together with any castings that fall into the bottom tray, interfere with the movement of liquid to exit the tray through the tap.

There is a need to address the above, and/or at least provide a useful alternative.

SUMMARY OF THE INVENTION

The present invention provides a housing for a worm farm, the housing comprising:

a composting cavity that, in use of the housing, is to contain worms, bedding material and/or organic waste, the composting cavity being defined by a floor having openings through which castings can pass, and one or more side walls that extend around the floor;

a support structure for supporting the floor and the side walls above a ground surface;

a cover that is to locate on the side walls and extend over the composting cavity, and is movable to enable access to the composting cavity; and a castings receptacle that is movable between an operative position, in which the castings receptacle is positioned beneath the floor to create a castings cavity for receiving material that falls from the composting cavity through the openings, and at least one displaced position, in which the castings cavity is accessible to enable removal of castings.

In certain embodiments, when in the operative position, the castings receptacle is suspended beneath the floor.

The castings receptacle can be at least partially lowered as it is moved from the operative position into the at least one displaced position.

Preferably, in the at least one displaced position, the castings cavity is accessible by an opening formed beneath the side wall.

In some embodiments, the castings receptacle is securable to the side walls and/or support structure of the housing.

Preferably, the castings receptacle, and side walls and/or support structure have complementary fasteners to enable the castings receptacle to be secured to the side walls and/or support structure. In one embodiment, the complementary fasteners include strips of hook and loop material.

The castings receptacle can include a flexible sheet material. Preferably, the sheet material is substantially water impermeable.

In some embodiments, the support structure is configured such that when the castings receptacle is in the operative position, a gap is provided between the ground surface and the castings receptacle.

Preferably, the castings receptacle has an aperture through which to discharge liquid that percolates through bedding material in the composting cavity, and through castings in the castings cavity. More preferably, the aperture is located centrally within the castings receptacle.

In embodiments in which the castings receptacle includes a flexible sheet with an aperture, the housing further comprises a weight that is to be placed on or near the aperture to create a sump-like shape in the flexible sheet, whereby liquid propagates towards the aperture. The weight can be in the form of a ballast receptacle, such as a pouch in which pebbles can be placed. The pouch is preferably made of an open weave fabric or mesh material.

In some embodiments, the support structure includes legs that support the side walls and/or floor above the ground surface.

The support structure can include lower bracing members that extend between the legs of the housing proximate to the lower end of the legs.

In certain embodiments, the cover is securable to the side walls by complementary fasteners. In one form, the complementary fasteners include strips of hook and loop material.

The cover can be made of a flexible sheet material. Preferably, the cover is made of an open weave fabric or mesh material.

In some embodiments, the floor includes a plurality of bars with gaps between the bars to provide the openings in the floor. In some forms, the bars can be spaced apart. The bars can be parallel and extend between two primary bearing members that are supported by the support structure. Preferably, the gap between adjacent bars is such that castings can pass through the gaps, and such that bedding material and/or organic material can be retained in the composting cavity.

In some alternative embodiments, the floor includes:
two primary bearing members;
two sets of spaced apart fingers, with each set extending from a respective one of the primary bearing members; and
a plurality of mating tubes that each receive at least one of the free ends of two opposing fingers in the sets, such that when the floor is assembled the spaced apart fingers and mating tubes form a plurality of spaced apart elongate members,
wherein gaps between the elongate members provide the openings in the floor.

Preferably, the gap between adjacent elongate members is such that castings can pass through the gaps, and such that bedding material and/or organic material can be retained in the composting cavity.

The floor may also include two secondary bearing members that are generally perpendicular to the primary bearing members.

The housing can have four side walls, such that the floor has a generally rectangular in shape.

In certain embodiments, each side wall includes a top rail at an upper edge of the side wall, and a bottom rail, and sheet material that extends at least between top and bottom rails.

The housing may also include pairs of interconnectable brackets to connect the top rails to the support structure, wherein one of the brackets in each pair is mounted to end of one of the top rails, and the other bracket in the respective pair is mounted on the support structure.

The present invention can also provide a kit comprising a plurality of components that, when assembled, form a housing for a worm farm as previously described.

The present invention also provides a planter box for mounting to a housing for a worm farm that has at least one side wall that includes a top rail at an upper edge of the side wall, and a bottom rail, the planter box including:
a base;
a back wall;
one or more additional walls that, with the back wall, surround the base so as to define a soil cavity; and
at least one tab that projects upwardly from the back wall,
wherein the back wall has a height that is approximately equal to the vertical spacing of the top and bottom rails, and wherein the planter box is mountable on the side wall with the tab located behind the top rail, and a portion of the base adjacent the back wall being supported on the bottom rail.

In one embodiment, the planter box has a flat base. In some alternative embodiments, the planter box has a stepped base, that provides an upper portion and a lower portion, and wherein, when the planter box is mounted on the side wall, the upper portion of the base is supported on the bottom rail.

BRIEF DESCRIPTION OF THE DRAWINGS

In order that the invention may be more easily understood, embodiments will now be described, by way of example only, with reference to the accompanying drawings, in which.

DETAILED DESCRIPTION

FIGS. 1 to 15 illustrate a housing 10 in accordance with a first embodiment of the present invention, that is suitable for use in containing a worm farm. The housing 10 has a composting cavity 12 that, in use of the housing 10, is to contain worms, and bedding material and/or organic waste that is to be composted by the worms. The composting cavity 12 is defined by a floor, and side walls 14 that extend around the floor. As will be evident from the figures, in this embodiment the composting cavity 12 has a rectangular footprint, and thus the housing 10 has four side walls 14.

The floor has openings through which castings can pass, as will be described in further detail below. In this particular embodiment, the floor is in the form of a grid 16, which will also be described in further detail below.

Figure 1:
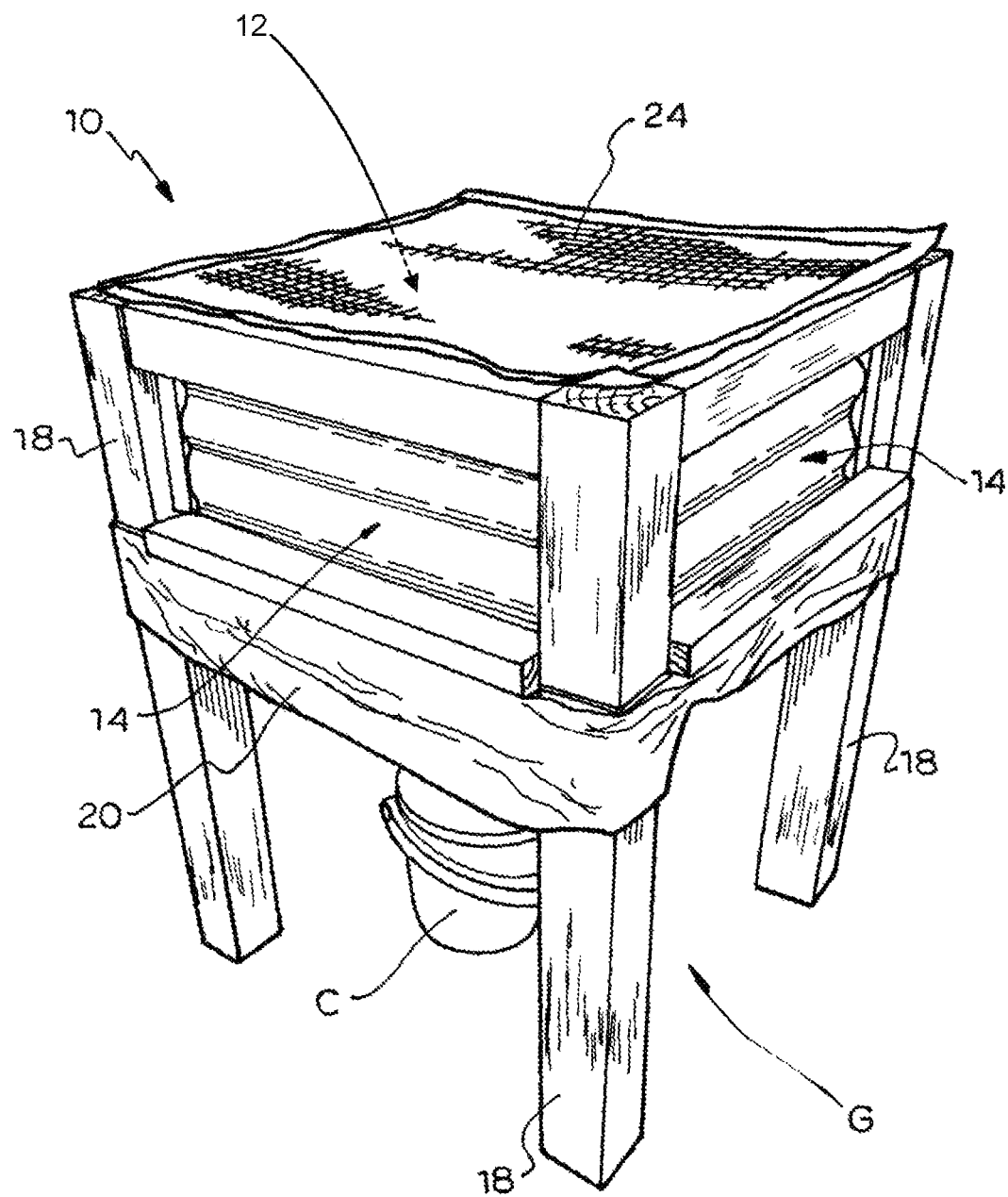
FIG. 1: is a perspective view of a housing for a worm farm according to a first embodiment of the present invention.
Figure 2:
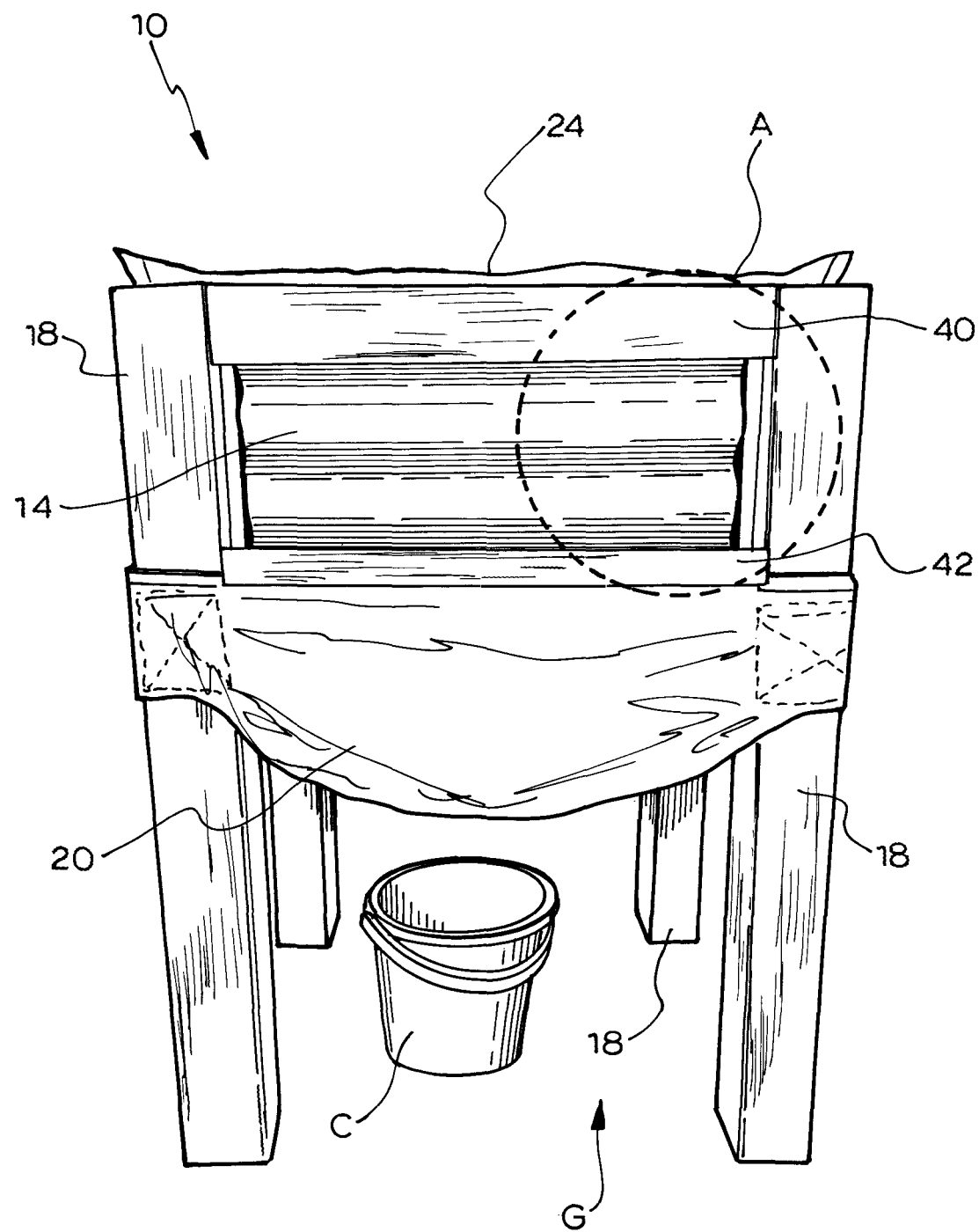
FIG. 2: is a front view of the housing of FIG. 1 showing the castings receptacle in an operative position.
Figure 3:
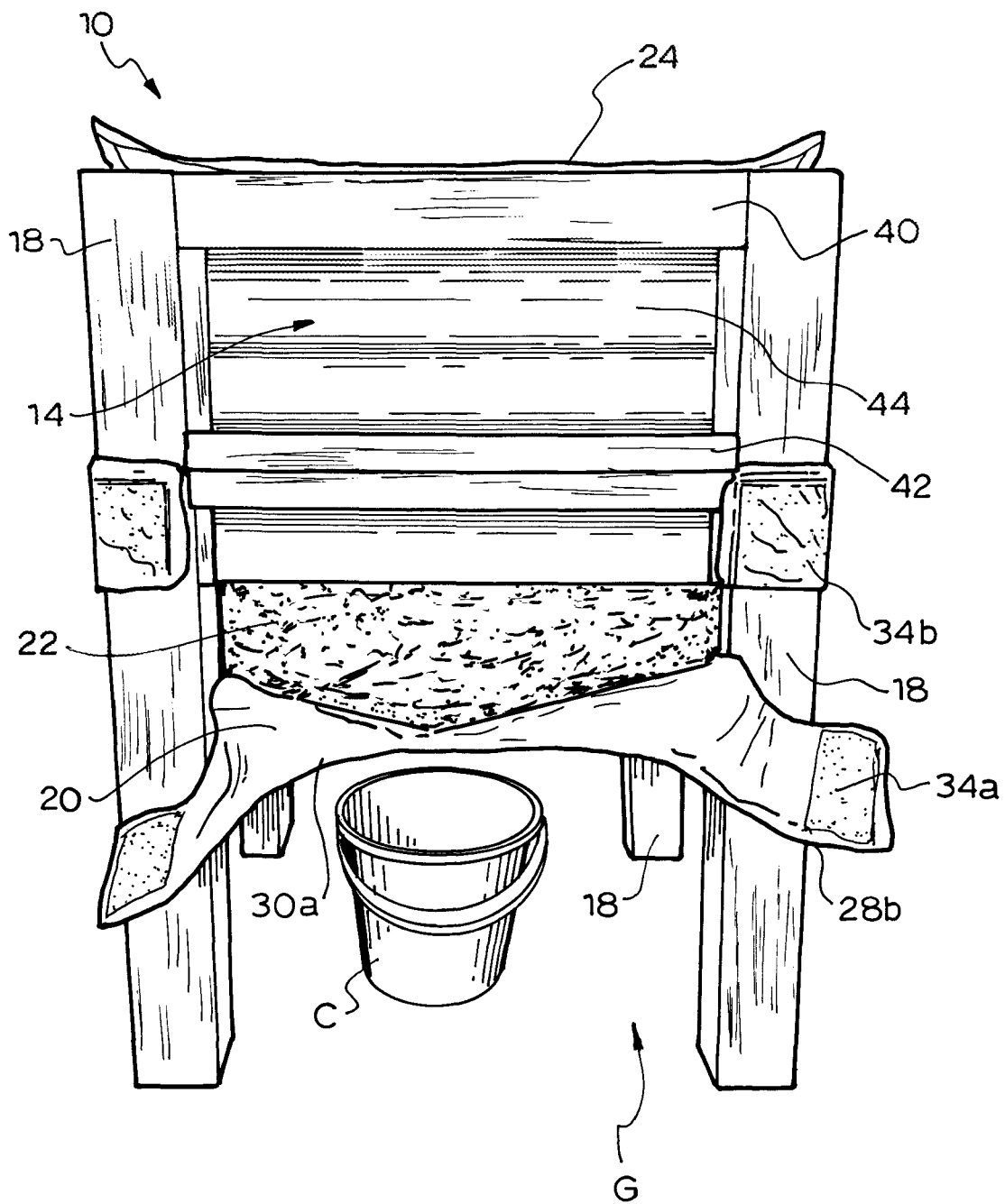
FIG. 3: is a front view of the housing of FIG. 1 showing the castings receptacle in a displaced position.

The housing 10 includes a support structure for supporting the grid 16 and the side walls 14 above a ground surface G. In this embodiment, the support structure is in the form of four legs 18 that support the side walls 14 and the grid 16, and rest on the ground surface G. Further, the housing 10 has a castings receptacle (hereinafter referred to as "catcher 20") that, in regular use, is in an operative position, in which the catcher 20 is positioned beneath the grid 16 to create a castings cavity 22 for receiving and retaining material (such as castings) that falls from the composting cavity 12 through the openings in the grid 16. FIGS. 1 and 2 show the housing 10 with the catcher 20 in the operative position. The catcher 20 can be moved into at least one displaced position, in which the castings cavity 22 is accessible to enable removal of castings. In this particular embodiment, the catcher 20 can be placed in many displaced positions, one of which is shown in FIG. 3. When the housing 10 is being used as a worm farm, the farmer can move the catcher 20 into a displaced position and directly remove castings from the castings cavity 22. As will be appreciated, the farmer is not required to lift any portion of the housing 10 in order to access the castings.

Figure 6:
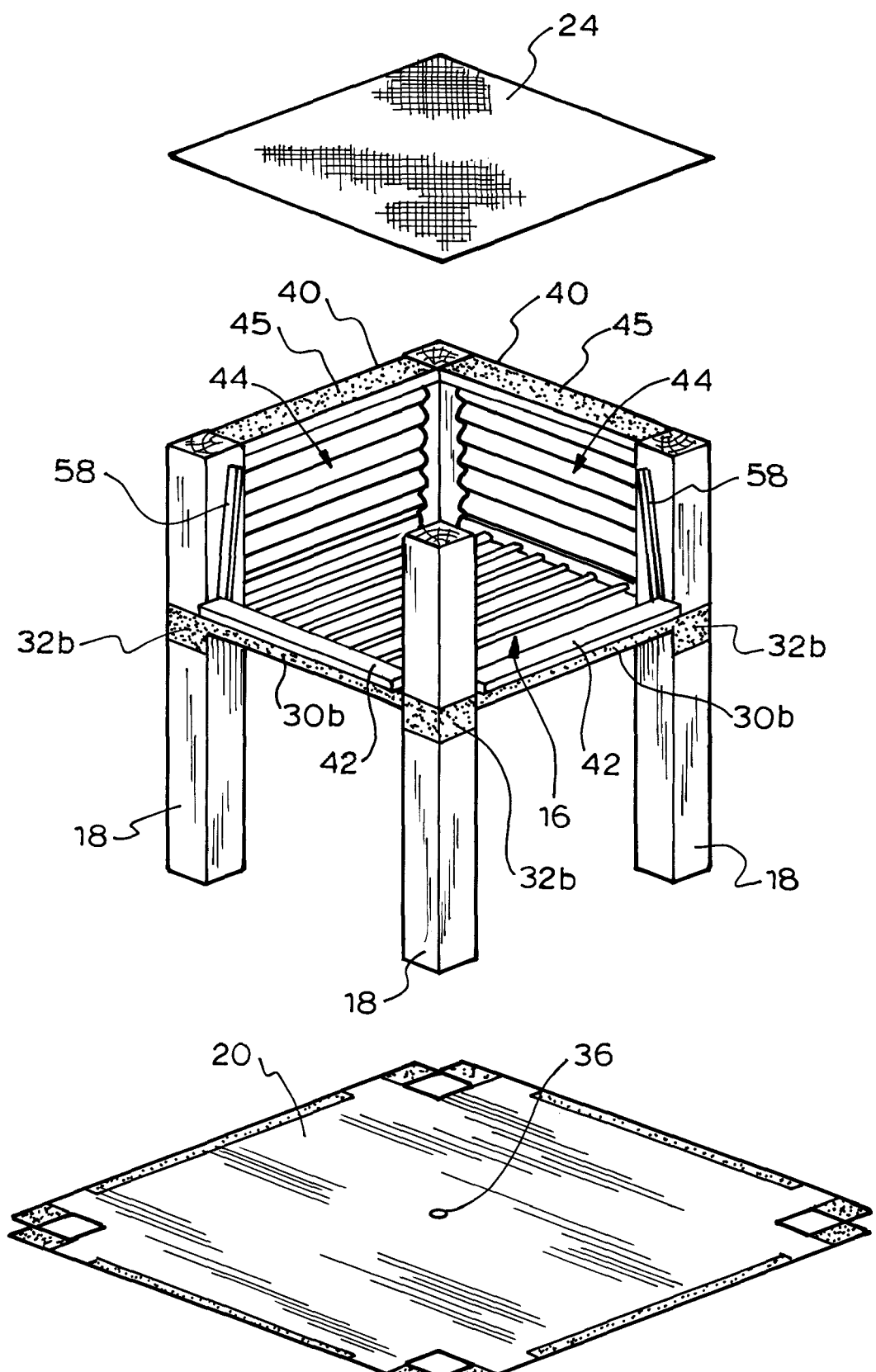
FIG. 6: is an exploded, partial view of the housing of FIG. 1.
Figure 9:
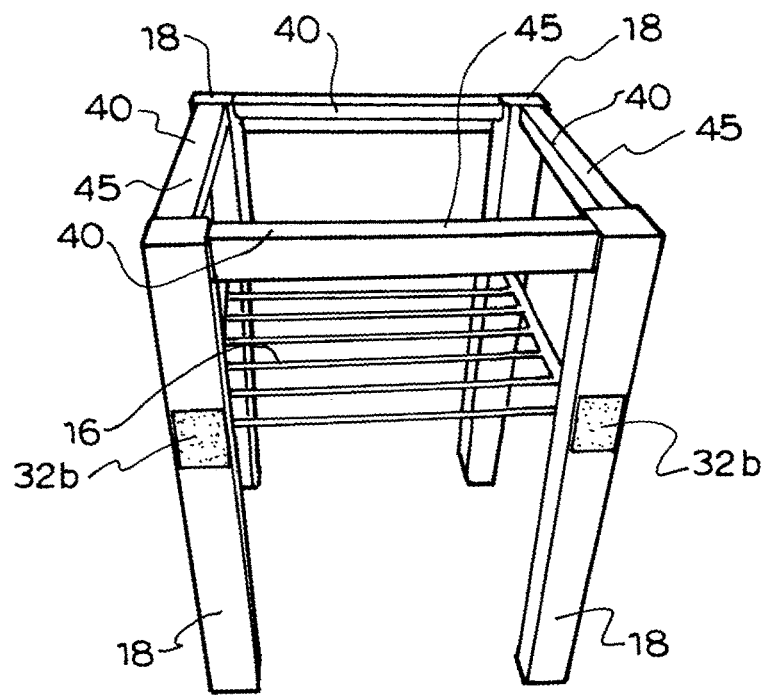
FIG. 9: is a first perspective view of a partially assembled housing according to the first embodiment.
Figure 10:
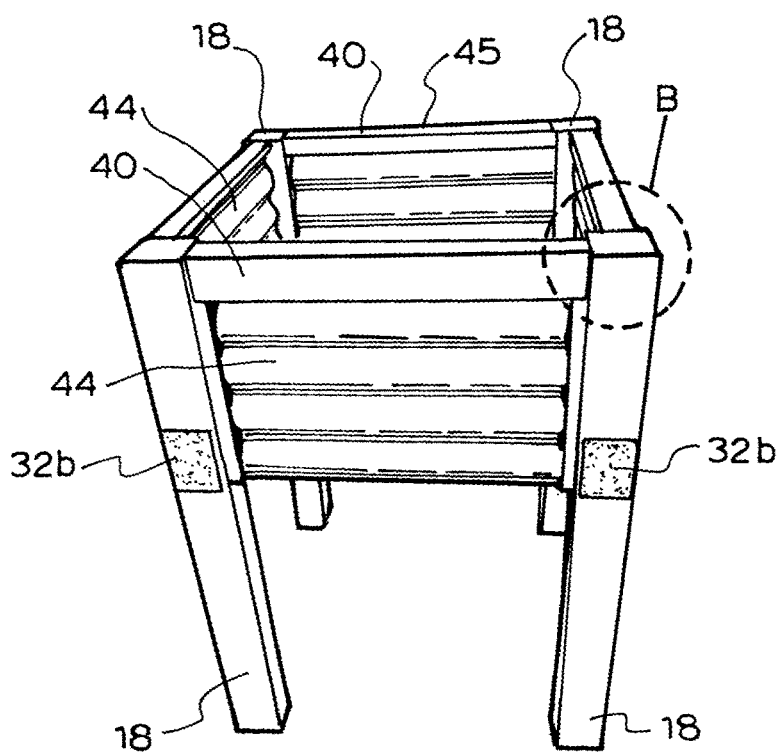
FIG. 10: is a second perspective view of a partially assembled housing according to the first embodiment.

A cover 24 locates on the side walls 14 and extends over the composting cavity 12. The cover 24 is removable to enable access to the composting cavity 12. In this particular embodiment, the cover 24 and upper edge of the side walls 14 have complementary strips of hook and loop material. FIGS. 6, 9 and 10 show strips 45 of hook material that are secured to the upper edge of the side walls 14.

The cover 24 can be made of a flexible sheet material, which in combination with the hook and loop materials, allows the cover 24 to be "peeled" back from the remainder of the housing 10 to provide access to the composting cavity 12. In this embodiment, the cover 24 is made of an open weave fabric, such as shade cloth material, which enables air exchange between the composting cavity 12 and the atmosphere around the housing 10. This aids in allowing air flow through the bedding material in the composting cavity 12. Further, rain falling on the cover 24 can reach the composting cavity 12, which helps keep the bedding material moist.

Figure 4:
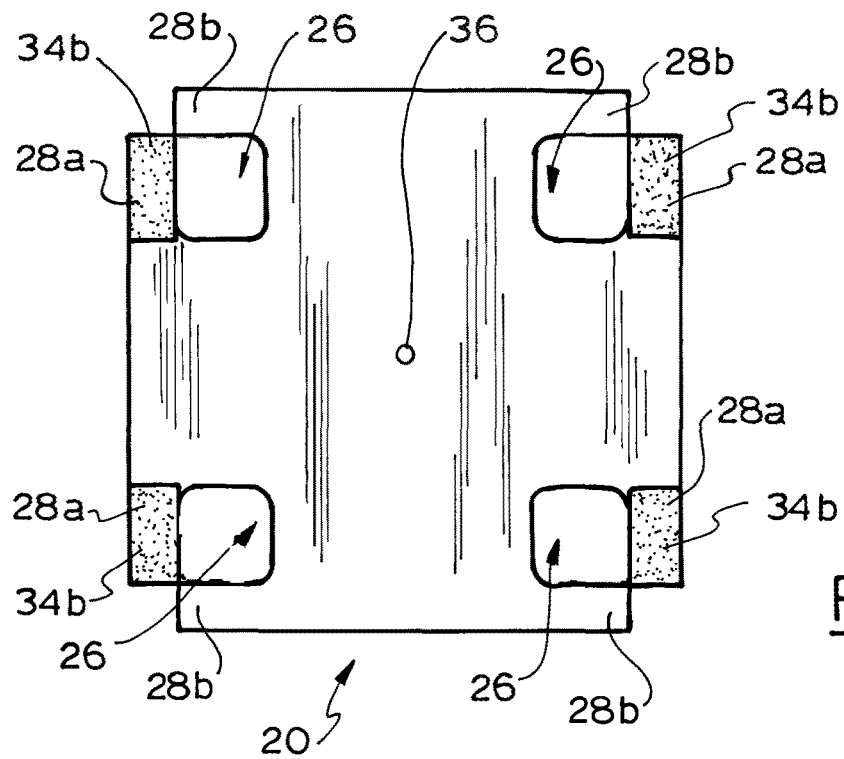
FIG. 4: is a plan view of the external side of the castings receptacle of the housing of FIG. 1.
Figure 5:
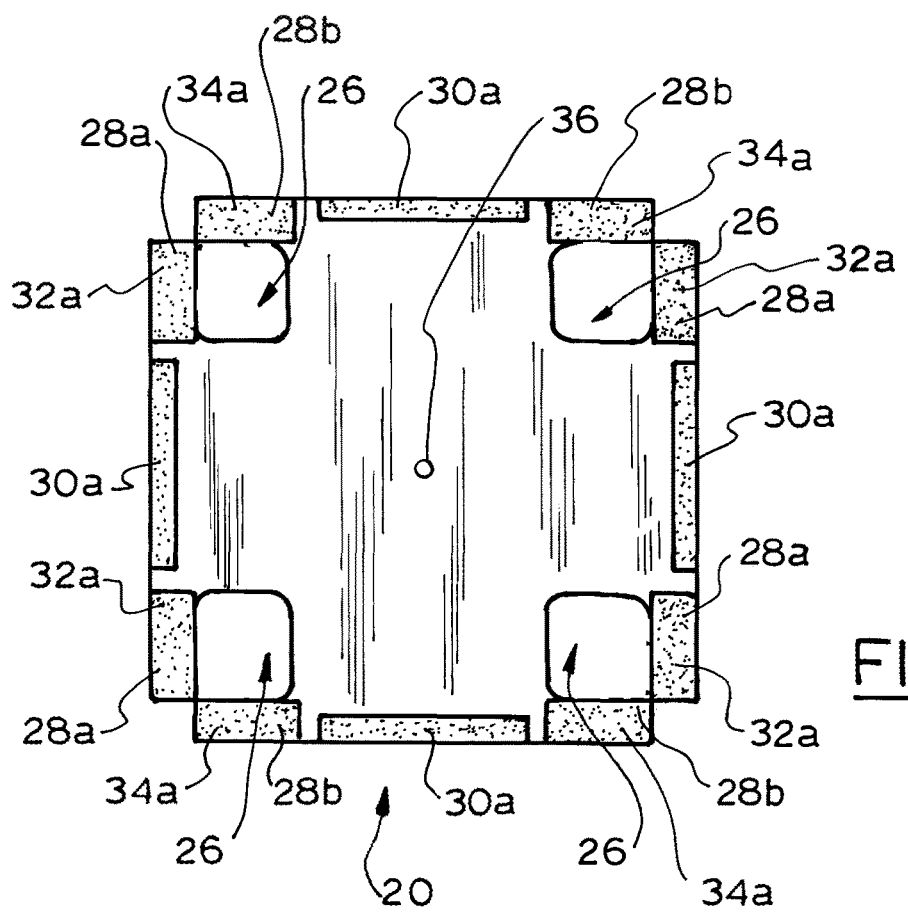
FIG. 5: is a plan view of the internal side of the castings receptacle of the housing of FIG. 1.

In this particular embodiment, the catcher 20 is made of a flexible sheet material, such as, for example, a plastics material, that is substantially impermeable to water. In one example, the catcher 20 is made of a high density woven polyethylene material, which can be UV resistant, and water impermeable. FIGS. 4 and 5 show the catcher 20 in further detail. When laid flat, the catcher 20 has a generally square periphery, and has an opening 26 at each corner. In addition, at each corner of the catcher 20 there is a pair of tabs 28a, 28b that extend transversely to one another along the respective opening 26.

The catcher 20 is securable to the side walls 14 and the legs 18 of the housing 10 in the operative and displaced positions by way of complementary fasteners. Further, the catcher 20 can be removed entirely from the walls 14 and legs 18. In this particular embodiment, the complementary fasteners are in the forms of strips of hook and loop material secured to the side walls 14, legs 18 and catcher 20.

As shown in FIGS. 4 to 6, the strips of hook and loop materials are secured the side walls 14, legs 18 and catcher 20 as described below, so as to enable the catcher 20 to be retained in the operative position:

1. four strips 30a of loop material are secured on the internal side—and adjacent to the peripheral edges—of the catcher 20, and these strips 30a fasten to strips 30b of hook material that are secured to the side walls 14;
2. four strips 32a of loop material are secured on the internal side—and on a first of the pair of tabs 28a at each corner of—the catcher 20, and these strips 32a fasten to strips 32b of hook material that are secured to the legs 18; and
3. four strips 34a of loop material are secured on the internal side—and on a second of the pair of tabs 28b at each corner of—the catcher 20, and these strips 34a fasten to strips 34b of hook material that are secured on the external side—and on the first of the tabs 28a at each corner of—the catcher 20.

The strips of hook and loop materials (30a, 30b, 32a, 32b, 34a, 34b) can be progressively and/or partially undone, or repositioned on one another to enable the catcher 20 to be lowered from the operative position, and placed into various displaced positions. As will be apparent from the Figures, when the catcher 20 is in the operative position, the catcher 20 is suspended beneath the grid 16. The castings cavity 22 is visible in FIG. 3, and is made accessible by an opening formed beneath the bottom edge of the side wall 14, and the catcher 20. In this embodiment, the catcher 20 is partially lowered as it is moved from the operative position into displaced positions, and this provides openings of various sizes through which to access to the castings cavity 22.

As shown in FIGS. 4 to 6, the catcher 20 also has an aperture 36 that is located centrally within the sheet. In addition, the housing 10 includes a weight that is to be placed on or near the aperture 36 during setup of the housing 10 to create a sump-like shape in the catcher 20. Liquid that percolates through bedding material in the composting cavity 12, and then through castings in the castings cavity 22, will ultimately reach the catcher 20. The sump-like shape formed in the catcher 20 by the weight causes this percolated liquid to migrate towards the central aperture 36 where it is discharged for collection.

As shown most clearly in FIGS. 1 to 3, the housing 10 is arranged such that configured such that when the catcher 20 is in the operative position, a gap is provided between the ground surface and the catcher 20. In this particular embodiment, this gap is achieved by the length of the legs 18. A container, such as a bucket C, can be placed on the ground G beneath the catcher 20 to collect liquid (the "worm tea") that is discharged through the aperture 36.

In this particular embodiment, the weight is in the form of a ballast receptacle, such as a pouch 38, into which pebbles can be placed. The pouch 38 is made of an open weave or mesh material with a closure of hook and loop material at its opening. The pouch 38 filled with pebbles allows liquid to readily pass therethrough as it moves to the aperture 36. Further, the pouch 38 inhibits castings from clogging or passing through the aperture 36.

Figure 13:
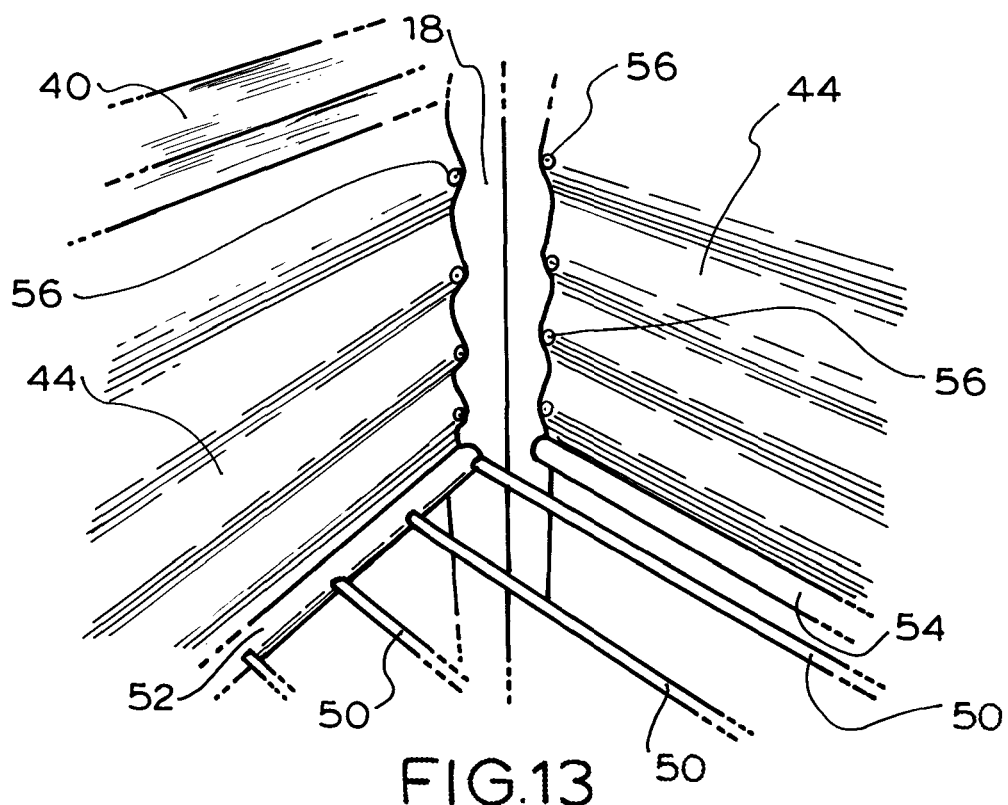
FIG. 13: is an internal perspective view of the housing of FIG. 1.
Figure 14:
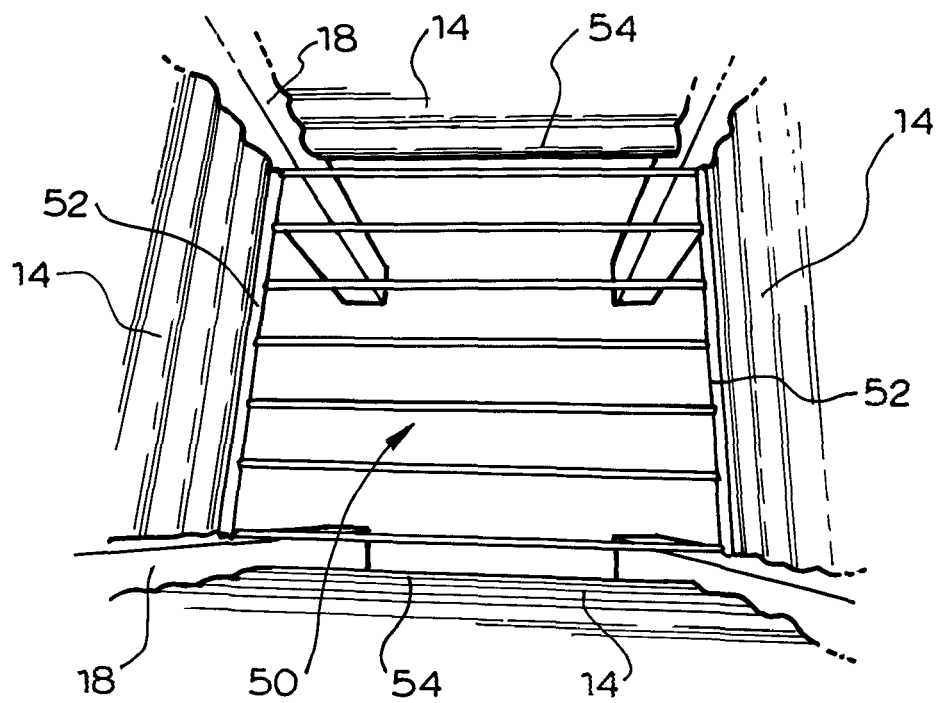
FIG. 14: is an internal plan view of the housing of FIG. 1.
Figure 15:
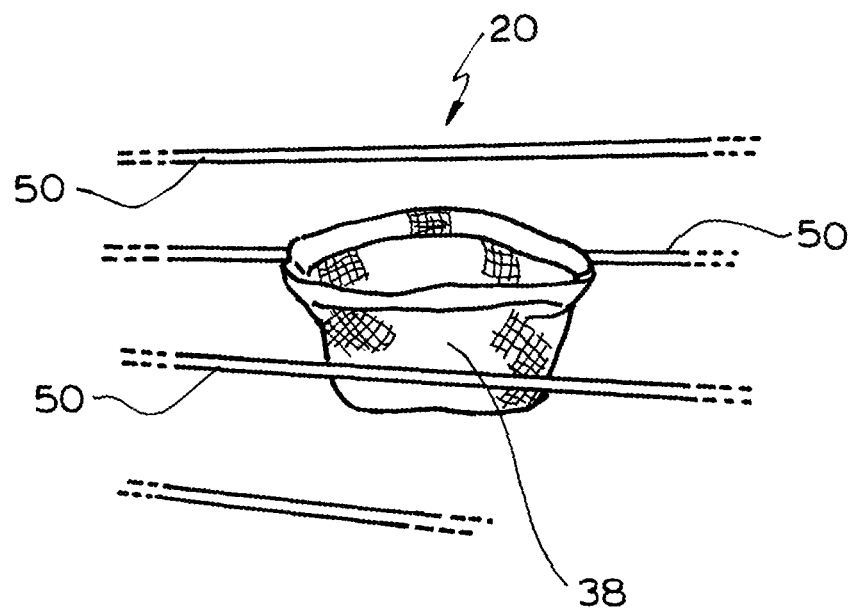
FIG. 15: is a view of the ballast container of the housing of FIG. 1.

The grid 16 of the housing 10 is shown in FIGS. 9, 13 and 14. In this particular embodiment, the grid 16 has spaced apart bars 50 with gaps between the bars 50; the gaps providing the openings within the grid 16. The bars 50 are parallel and extend between two primary bearing members 52 that are supported by the legs 18. The gap between pairs of adjacent bars 50 is sufficiently wide that castings can pass through the gaps, and is also sufficiently narrow that bedding material and/or organic material can be retained in the composting cavity 12. The gaps between the bars 50 are in the range of approximately 60 mm to 140 mm.

As will be understood by the person skilled in the art, in an operating worm farm the bedding material within the composting cavity 12 is moist and has the capacity to bind to itself. However, worms moving through the bedding material disrupts the binding capacity, which can dislodge some of the bedding material at the base of the composting cavity 12. By virtue of the composting process, bedding material at the base of the composting cavity 12 in an operating worm farm is generally a castings, and thus it is mostly castings that fall through the grid 16.

The grid 16 also includes include two secondary bearing members 54 that are generally perpendicular to the primary bearing members 52. As will be evident from FIGS. 13 and 15, the primary and second bearing members 52, 54 are received within blind holes in the legs 18, and this construction assists retaining the housing 10 in its assembled form.

Figure 11:
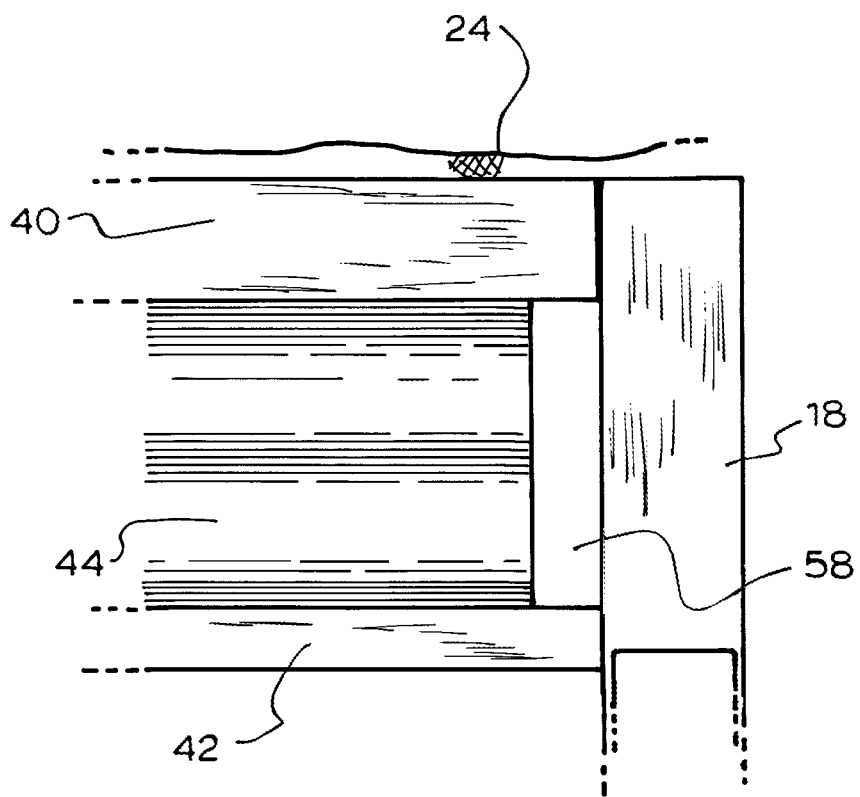
FIG. 11: is an enlarged schematic view of region A in FIG. 2.
Figure 12:
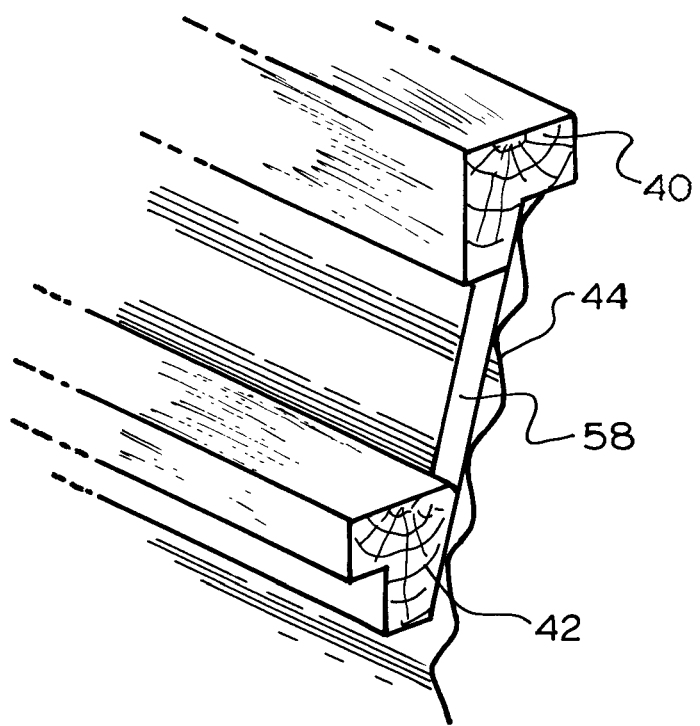
FIG. 12: is a schematic perspective view of the side wall as shown in FIG. 11.

As shown most clearly FIGS. 11 and 12, each of the four side walls 14 has an top rail 40, a bottom rail 42, and sheet material, which in this embodiment is in the form of corrugated sheet 44 of galvanized steel. In this embodiment, the top rail 40 extends along the upper edge of the corrugated sheet 44, and the bottom rail 42 extends across the sheet 44 intermediate of the upper and lower edges. The sheet 44 provides an enclosure to the sides of the composting cavity 12 and extends below the bottom level of the grid 16. The ends of the top and bottom rails 40, 42 are secured to adjacent pairs of legs 18, and provide lateral support to the sheet 44 within the respective side wall 14. The strips 45 of hook material are secured to the upper surface of the top rails 40.

Figure 7:
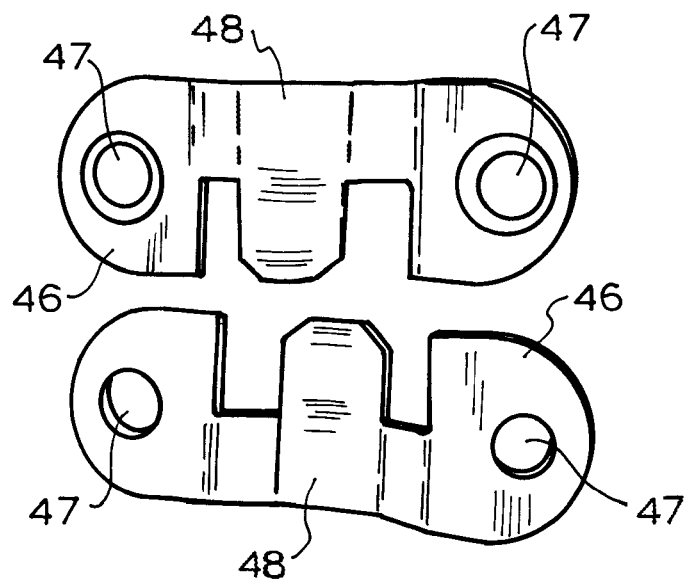
FIG. 7: is a plan view of a pair of concealed flush mount brackets of the housing of FIG. 1.
Figure 8:
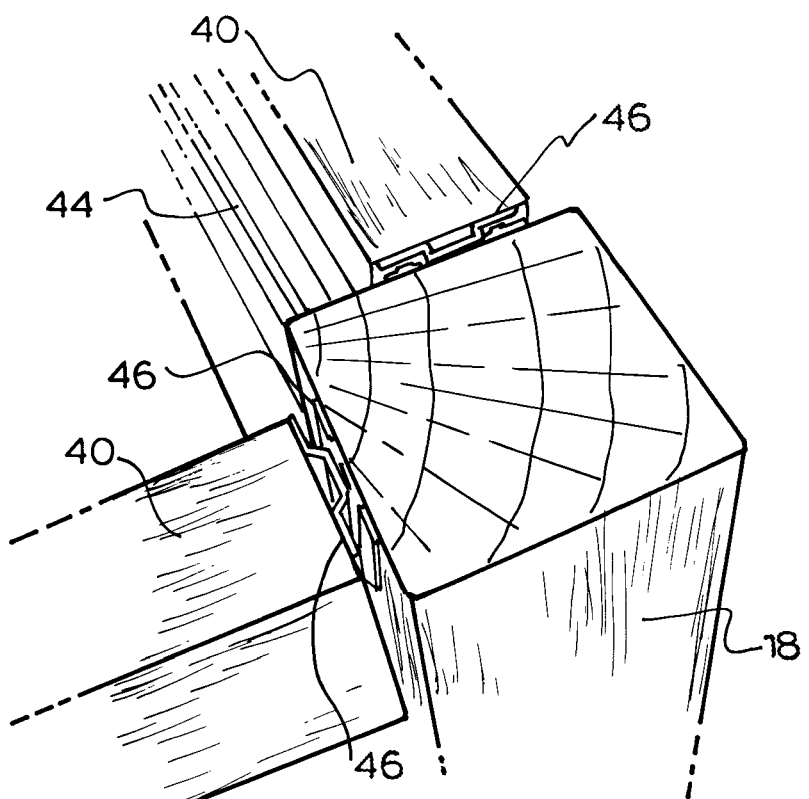
FIG. 8: is an enlarged view of region B in FIG. 10.

As shown in FIGS. 7 and 8, the housing 10 has uses pairs of concealed flush mount brackets 46 that are secured to the upper side faces of the legs 18, and to the ends of the top rails 40. To this end, each bracket 46 has a pair of holes 47 through which a fastener is to pass to fix the bracket 46 to the leg 18 or rail, as required. Each of the brackets 46 has a tongue 48, and pairs of the brackets 46 interconnect to one another by interleaving the tongues 48, in a manner evident from FIG. 8. Each bracket 46 is contoured, so as to facilitate the interconnecting.

In this particular embodiment, the bottom rails 42 are secured to the legs by fasteners (not shown) that each extend upwardly through the end of one of the bottom rails 42 and into the adjacent leg 18. As previously described, the strips 30*b* of hook material are secured to the side walls 14; in this particular embodiment, the strips 30*b* are secured to the bottom rails 42. In this embodiment, the top and bottom rails 40, 42 are also configured to provide support to a planter box, as described in further detail below.

In each side wall 14, the corrugated sheet 44 is secured in position by screw fasteners 56 that extend through the sheet 44 adjacent its edge, and into the leg 18 that is adjacent that edge, as is evident from FIG. 13. The upper edge of the corrugated sheet 44 is concealed behind the top rail 40, as is shown in FIG. 12. The housing 10 also includes fascia strips 58 that project from slots in the side faces of the legs 18. Each fascia strip 58 overlaps with a lateral edge of one of the corrugated sheets 44. As will be appreciated, when the catcher 20 is in its operative position, the lower edge of the corrugated sheet 44 is concealed behind the catcher 20.

The housing 10 of this embodiment can be arranged to be constructed from a number of pre-formed components, for example from a kit, or flat-pack arrangement. It is common for products that are sold in flat-pack form to be packaged in a cardboard box. Composting worms are known to consume wetted cellulose material, and the packaging materials provide a convenient base material to be laid on the grid 16 prior to placing bedding material in the composting cavity 12.

Figure 16:
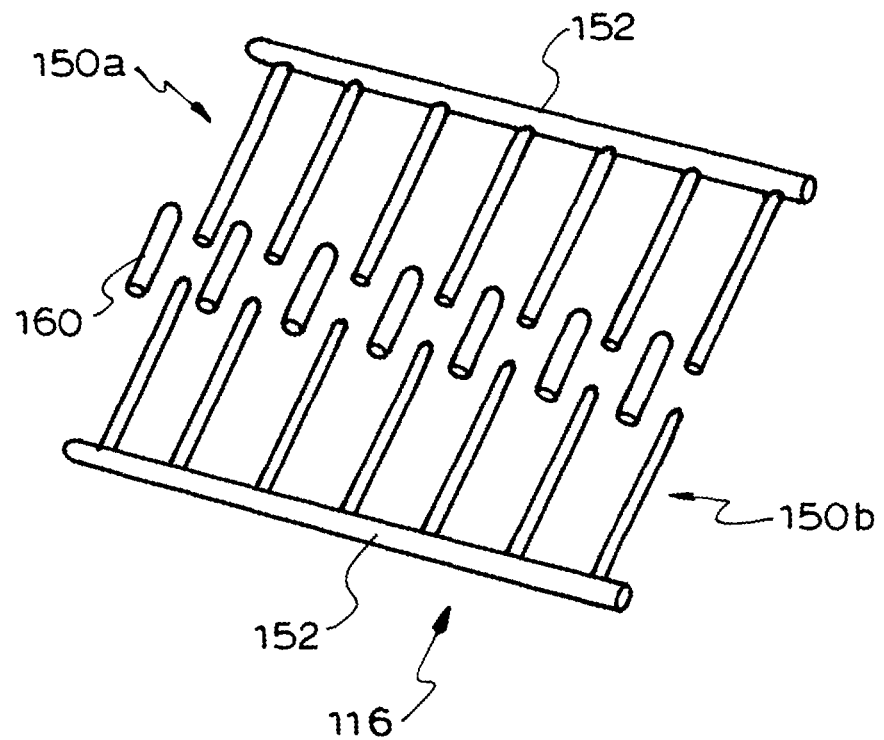
FIG. 16: is a perspective view of a bedding material support of a housing for a worm farm according to a second embodiment of the present invention.

FIG. 16 shows a floor of a housing according to a second embodiment of the present invention. In this embodiment of the housing, the floor is in the form of a grid 116, and housing of this second embodiment is otherwise identical to that of the first embodiment. For the sake of brevity, only the grid 116 is described.

In this embodiment, the grid 116 has two primary bearing members 152, and two secondary bearing members (not shown). The grid 116 has two sets of spaced apart fingers 150*a*, 150*b*, with each set extending from a respective one of the primary bearing members 152. Mating tubes 160 each receive free ends of two opposing fingers in the sets. When the grid 116 is assembled, the spaced apart fingers 150*a*, 150*b* are located within the mating tubes 160 to form spaced apart elongate members, with gaps therebetween to form the grid structure. The grid 116 is particularly useful in embodiments in which the housing is to be sold in flat-pack form.

In a similar but alternative configuration, the mating tubes of the grid can be connected to, or integral with, the ends of one of the sets of fingers.

In some alternative constructions of a housing for a worm farm in accordance with the present invention, some or all of the components may be formed of plastics materials that interconnect during assembly and/or use. For example, the support structure, side walls, floor, cover and/or catcher can be made of moulded from plastics materials using injection moulding, rotary moulding, or the like.

Figure 17:
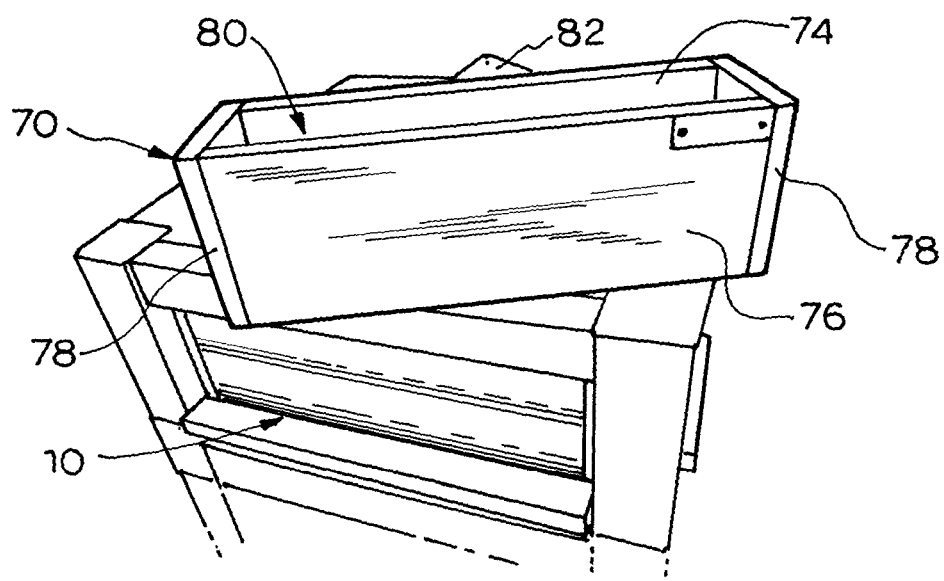
FIG. 17: is a front view of a planter box that is mountable on a housing for a worm farm according to an embodiment of the present invention.
Figure 18:
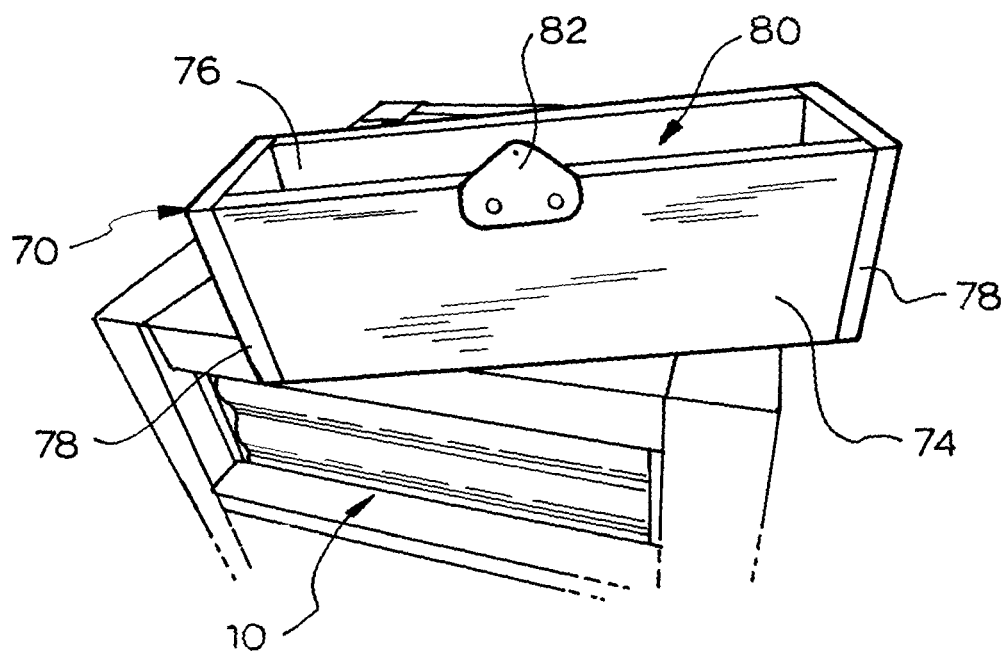
FIG. 18: is a rear view of the planter box of FIG. 17.
Figure 19:
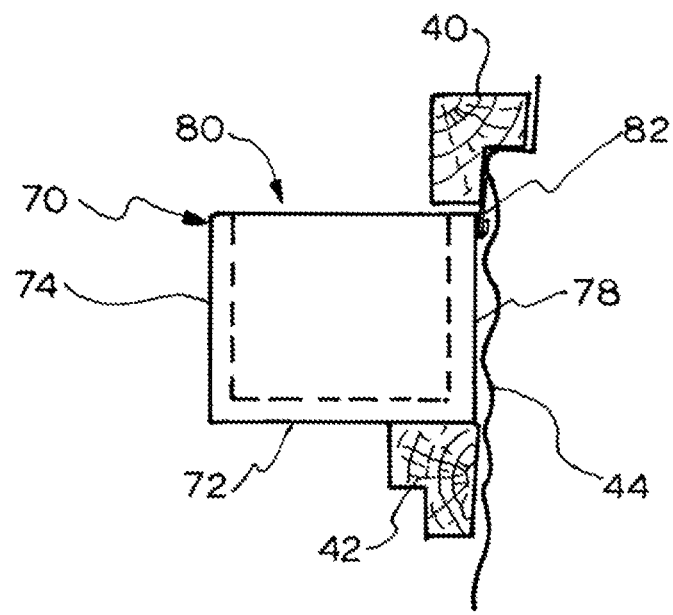
FIG. 19: is a schematic view showing the planter box of FIG. 17 mounted on the housing of FIG. 1.

FIGS. 17 to 19 show a planter box 70 that is suitable for mounting to a housing, such as the housing 10 of the first described embodiment. The planter box 70 has a base 72, and a back wall 74. In this embodiment, the box 70 also has a front wall 76 and two side walls 78. The back, front and side walls 74, 76, 78 surround the base 72 so as to define a soil cavity 80, in which soil and plants can be contained. The back wall 74 has a height that is approximately equal to the vertical spacing of the top and bottom rails 40, 42 of the housing 10.

The planter box 70 has a tab 82 that projects upwardly from the back wall 74. As is evident from FIG. 19, the planter box 70 is mountable on the side wall 14 of the housing 10, with the tab 82 located behind the top rail 40, and a portion of the base 72 adjacent the back wall 74 being supported on the bottom rail 42.

Figure 20:
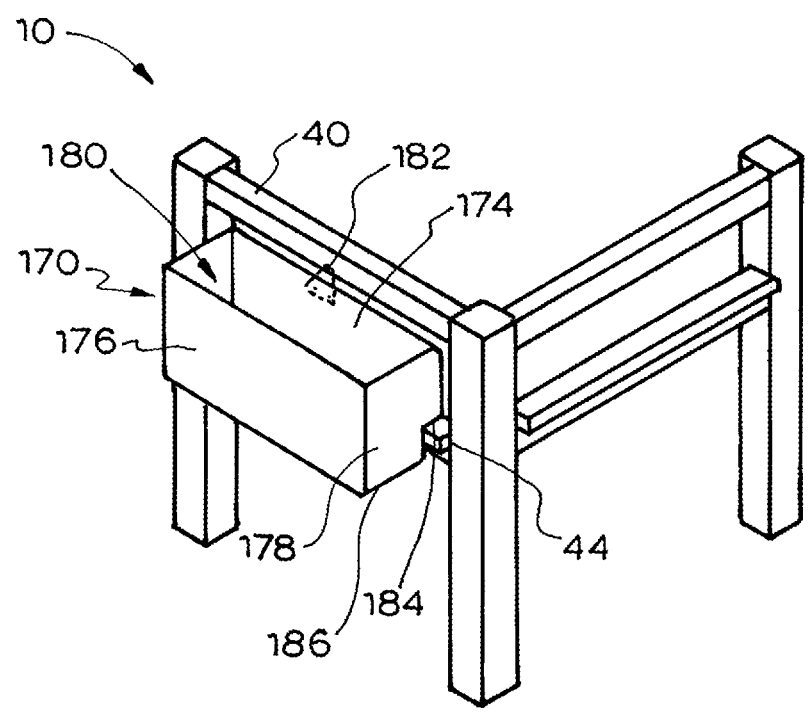
FIG. 20: is a schematic view showing another planter box mounted on a housing for a worm farm according to an embodiment of the present invention.

In the embodiment illustrated in FIGS. 17 to 19, the planter box 70 has a flat base 72. FIG. 20 shows a planter box 170 of an alternative embodiment that is substantially similar to the planter box 70. In FIG. 20, the features of the planter box 170 that are substantially similar to those of the planter box 70 have the same reference numeral with the prefix "1". The principal difference is that the planter box 170 has a stepped base 172 that forms an upper portion 184 and a lower portion 186. When the planter box 170 is mounted on the side wall 14, the upper portion 184 of the base 172 is supported on the bottom rail 42.

The planter box 170 has the advantage of being capable of growing plants that grow deeper root systems, when compared with the planter box 70.

As will be appreciated from the Figures, the housing 10 of the illustrated embodiment has a square footprint. It will be appreciated that in some alternative embodiments, housings in accordance with the present invention may have a footprint of other shapes, including circular, rectangular, triangular, etc. Further, the catcher 20 of the housing 10 in this embodiment forms a single sump-like shape. In some alternative embodiments, the housing can be configured to have two or more sump-like shapes. Consequently, the housing can have separate, or at least partially separate castings cavities. The multiple sump-like shapes may be formed from one, or more than one, flexible sheet. For instance, a housing with a rectangular footprint can be constructed with two or more sump-like shapes. These can be formed from a single catcher, or multiple separate catchers.

Figure 21:
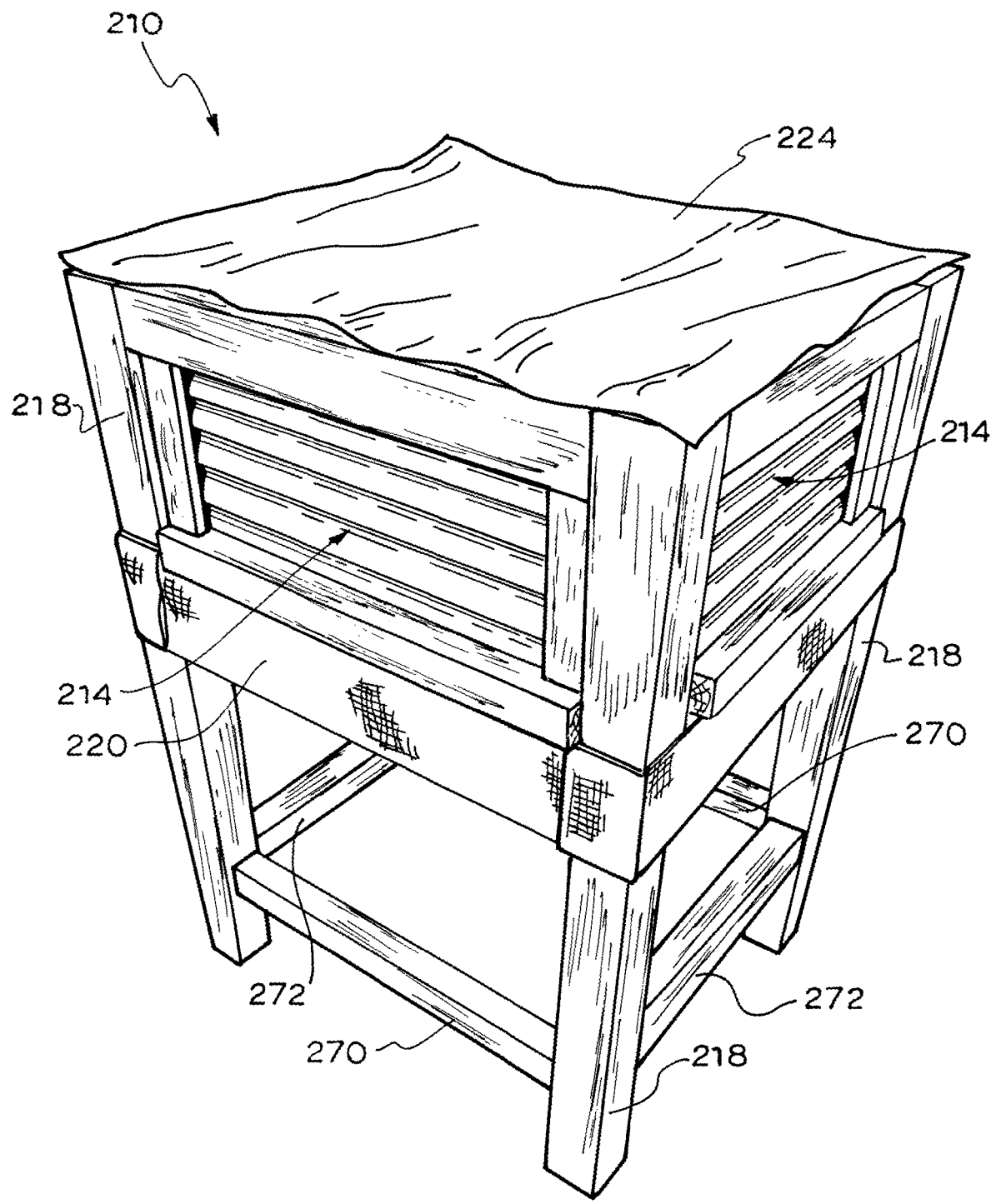
FIG. 21: is a perspective view of a housing for a worm farm according to a fourth embodiment of the present invention.
Figure 22:
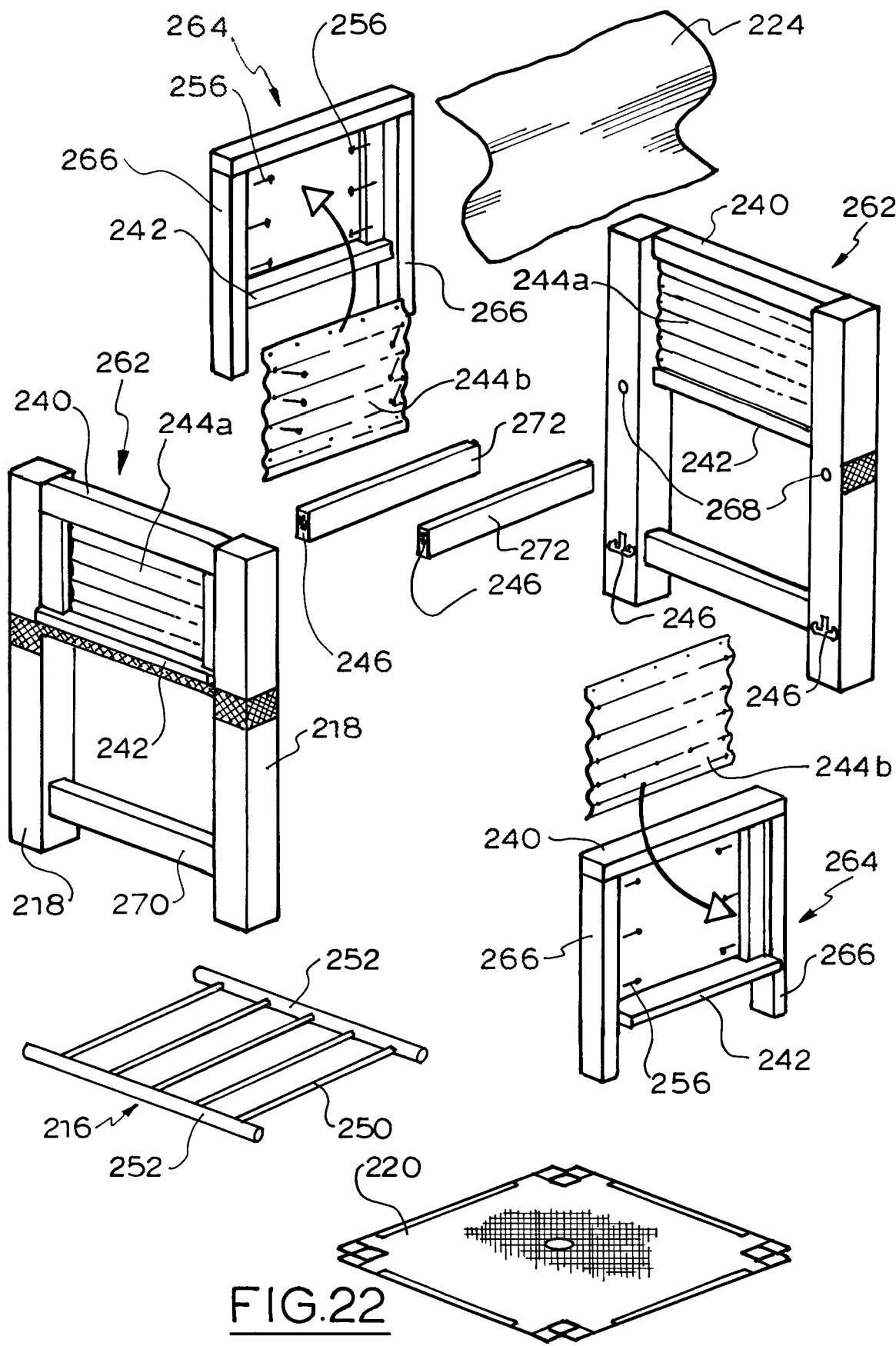
FIG. 22: is a schematic view of the housing of FIG. 21 in a disassembled state.

FIGS. 21 and 22 illustrate a housing 210 in accordance with another embodiment of the present invention, that is suitable for use in containing a worm farm. The housing 210 is substantially similar to the housing 10 of FIG. 1. In FIG. 21, the features of the housing 210 that are substantially similar to those of the housing 10 have the same reference numeral with the prefix "2".

As shown in FIG. 22, the housing 210 is constructed in a manner that is particularly suitable for being sold in a flat-pack form, for subsequent assembly. To this end, the housing 210 includes two primary sub-frames 262, and two secondary sub-frames 264. Each primary sub-frame 262 includes two pairs of legs 218, a top rail 240, a bottom rail 242, and a corrugated sheet 244a (that provides the sheet material of the respective side wall 214. Each secondary sub-frame 264 includes a top rail 240 and a bottom rail 242 that are interconnected by vertical members 266 to form a rectangular structure.

In this embodiment, the grid 216 includes parallel spaced apart bars 250 that extend between two bearing members 252. In the assembled housing 210, the ends of the bearing members 252 are located in blind holes 268 that are formed in the legs 218.

Corrugated sheets 244b are provided that are each secured to one of the secondary sub-frames 264 to form side walls 214. In some embodiments, each corrugated sheet 244a, 244b of the housing 210 can be provided with a rubber surround material on edges that are exposed to manual contact during assembly and/or use of the housing 210. To this end, the corrugated sheets 244a each have rubber surround material extending along only the bottom peripheral edge, and the corrugated sheets 244b have rubber surround material extending around all four peripheral edges.

The housing 210 includes four lower bracing members that extend between the legs 218 to maximize the stability of the housing 210. Two of the lower bracing members 270 are secured to legs 218 within the primary sub-frame 262. The other two lower bracing members 272 have a pair of concealed flush mount brackets 246 (of the type shown in FIG. 7) secured to the opposing ends. Side faces of the legs 218, have complementary concealed flush mount brackets 246.

The housing 210 can be assembled from its flat-pack form in the following procedure:
1. each secondary sub-frame 264 is secured to a first of the primary sub-frames 266 by inserting screw fasteners 256 through the vertical members 266 and into legs 218 of the first primary sub-frame 262;
2. grid 216 is positioned such that ends of the bearing members 252 are located in the blind holes 268 of the first primary sub-frame 262;
3. each secondary sub-frame 264 is secured to a second of the primary sub-frames 266, again by inserting screw fasteners 256 through the vertical members 266 and into legs 218 of the second primary sub-frame 262, whilst simultaneously locating ends of the bearing members 252 in the blind holes 268 of the second primary sub-frame 262;
4. the two lower bracing members 272 are interconnected with the primary sub-frames 262 by interconnecting the respective pairs of concealed flush mount brackets 246;
5. corrugated sheets 244b are secured to the secondary sub-frames 262 using screw fasteners; and
6. The catcher 220 and cover 224 can be installed, as appropriate.

It will be appreciated that the assembly procedure described above is merely an example, and that the components of the housing 210 can be assembled following alternative procedures.

In this embodiment, the flat-pack form provides a kit from which the housing 210 can be assembled. In this particular embodiment, the components of the kit include at least:
  two primary sub-frames 262;
  two secondary sub-frames 264;
  two corrugated sheets 244b;
  two lower bracing members 272;
  a grid 216;
  catcher 220 and cover 224; and
  fasteners (such as screw fasteners 256), as required.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention has been described by way of non-limiting examples only and many modifications and variations may be made thereto without departing from the spirit and scope of the invention.

The invention claimed is:
1. A housing for a worm farm, the housing comprising:
  a composting cavity that, in use of the housing, is to contain one or more of: worms, bedding material, and organic waste, the composting cavity being defined by a floor having openings through which castings can pass, and one or more side walls that extend around the floor;
  a support structure for supporting the floor and the side walls above a ground surface, the support structure including first fasteners secured to the side walls;
  a cover that is to locate on the side walls and extend over the composting cavity, and is movable to enable access to the composting cavity; and
  a castings receptacle that includes flexible sheet material, and second fasteners that are secured adjacent peripheral edges of the flexible sheet material, the first fasteners and the second fasteners being complementary to one another, the castings receptacle being movable between:
    an operative position, in which the first fasteners and the second fasteners are releasably secured to one another to secure the castings receptacle to the side walls, thereby suspending the castings receptacle beneath the floor and creating a castings cavity for receiving material that falls from the composting cavity through the openings, and at least one displaced position, in which the castings cavity is accessible to enable removal of castings, when the castings receptacle is in the at least one displaced position, the first fasteners and the second fasteners are partially undone or repositioned on one another such that the castings receptacle is lowered from the operative position, wherein the flexible sheet material of the castings receptacle defines an aperture through which to discharge liquid that percolates through bedding material in the composting cavity, and through castings in the castings cavity; and the support structure is configured such that when the castings receptacle is in the operative position, a gap is provided between the ground surface and the castings receptacle.

2. The housing according to claim 1, wherein the castings receptacle is at least partially lowered as it is moved from the operative position into the at least one displaced position.

3. The housing according to claim 1, wherein the aperture is located centrally within the castings receptacle.

4. The housing according to claim 1, wherein the sheet material is substantially water impermeable.

5. The housing according to claim 1, further comprising a weight that is to be placed on or near the aperture to create a sump-like shape in the flexible sheet, whereby liquid propagates towards the aperture.

6. The housing according to claim 1, wherein the support structure includes legs that support the floor above the ground surface.

7. The housing according to claim 1, wherein the cover is made of an open weave fabric or mesh material.

8. The housing according to claim 1, wherein the floor includes a plurality of spaced apart bars with gaps between the bars to provide the openings in the floor.

9. The housing according to claim 8, wherein the gap between adjacent bars is such that castings can pass through the gaps, and such that organic material can be retained in the composting cavity.

10. The housing according to claim 1, wherein each side wall includes a top rail at an upper edge of the side wall, and a bottom rail, and sheet material that extends at least between the top rails and the bottom rails.

11. The housing according to claim 10, further comprising pairs of interconnectable brackets to connect the top rails to the support structure, wherein one of the brackets in each pair is mounted to end of one of the top rails, and the other bracket in the respective pair is mounted on the support structure.

12. The housing according to claim 1, wherein the support structure includes legs that support the side walls above the ground surface.

* * * * *